(12) United States Patent
Khouri

(10) Patent No.: US 11,354,007 B2
(45) Date of Patent: Jun. 7, 2022

(54) DIAGRAM BASED VISUAL PROCEDURE NOTE WRITING TOOL

(71) Applicant: Olympus America, Inc., Center Valley, PA (US)

(72) Inventor: Rami H. Khouri, Catasauqua, PA (US)

(73) Assignee: Olympus America, Inc., Center Valley, PA (US)

( * ) Notice: Subject to any disclaimer, the term of this patent is extended or adjusted under 35 U.S.C. 154(b) by 32 days.

(21) Appl. No.: 14/680,384

(22) Filed: Apr. 7, 2015

(65) Prior Publication Data

US 2016/0299664 A1 Oct. 13, 2016

(51) Int. Cl.

| G06F 3/0481 | (2022.01) |
| G06F 3/04845 | (2022.01) |
| G16H 40/20 | (2018.01) |
| G16H 10/60 | (2018.01) |
| G16H 40/63 | (2018.01) |
| G06F 16/58 | (2019.01) |
| G16H 70/20 | (2018.01) |
| G16H 30/40 | (2018.01) |

(52) U.S. Cl.
CPC ........ *G06F 3/0481* (2013.01); *G06F 3/04845* (2013.01); *G06F 16/5866* (2019.01); *G16H 10/60* (2018.01); *G16H 30/40* (2018.01); *G16H 40/20* (2018.01); *G16H 40/63* (2018.01); *G16H 70/20* (2018.01)

(58) Field of Classification Search
CPC ............... G06F 3/0481; G06F 3/04817; G06F 3/04845; G06F 16/5866; G16H 40/20; G16H 10/60; G16H 40/63; G16H 30/00; G16H 30/20; G16H 30/40; G16H 70/20
See application file for complete search history.

(56) References Cited

U.S. PATENT DOCUMENTS

| 5,581,460 | A | * | 12/1996 | Kotake | ................... G16H 50/20 705/3 |
| 6,031,566 | A | | 2/2000 | Leo | |
| 6,208,344 | B1 | | 3/2001 | Holzman et al. | |
| 7,492,388 | B2 | | 2/2009 | Odlivak et al. | |
| 7,793,217 | B1 | * | 9/2010 | Kim | .................... G06F 19/3425 715/255 |
| 7,949,542 | B2 | * | 5/2011 | Hamiter | .................. G06Q 50/22 705/2 |
| 8,310,529 | B2 | | 11/2012 | Krupnick et al. | |
| 8,321,241 | B1 | | 11/2012 | Mansour et al. | |
| 8,560,968 | B1 | * | 10/2013 | Nair | .................... G06F 19/3406 715/810 |
| 8,615,115 | B2 | | 12/2013 | Iwase | |
| 8,661,401 | B1 | | 2/2014 | Ogami et al. | |

(Continued)

*Primary Examiner* — Kieu D Vu
*Assistant Examiner* — Blaine T Basom
(74) *Attorney, Agent, or Firm* — Scully, Scott, Murphy & Presser, P.C.

(57) ABSTRACT

A diagram based visual procedure note writing, in one aspect, presents an image representing a structure on a user interface display. A plurality of objects is presented on the user interface display. Responsive to an object being placed onto the image of the structure, metadata associated with the object is updated based on region information associated with a position where the object is placed onto the image. The updated metadata is presented on the user interface display. A note is composed based on the updated metadata.

15 Claims, 18 Drawing Sheets

(56) References Cited

U.S. PATENT DOCUMENTS

| | | | |
|---|---|---|---|
| 8,712,192 B2 | 4/2014 | Thota | |
| 8,744,147 B2* | 6/2014 | Torti | G16H 15/00 |
| | | | 382/128 |
| 8,753,199 B2 | 6/2014 | Velu | |
| 9,177,110 B1* | 11/2015 | Fram | G06F 19/3487 |
| 2002/0131625 A1* | 9/2002 | Vining | G16H 30/20 |
| | | | 382/128 |
| 2005/0065954 A1* | 3/2005 | Baratange | G06F 17/30327 |
| 2005/0114283 A1* | 5/2005 | Pearson | G16H 10/60 |
| | | | 706/50 |
| 2005/0137907 A1* | 6/2005 | Barski | G16H 40/20 |
| | | | 705/2 |
| 2008/0250070 A1* | 10/2008 | Abdulla | G06F 19/3406 |
| 2009/0171225 A1* | 7/2009 | Gadodia | G06F 19/3487 |
| | | | 600/508 |
| 2011/0082710 A1* | 4/2011 | Subash | G06F 19/322 |
| | | | 705/3 |
| 2013/0111380 A1 | 5/2013 | Parker et al. | |
| 2014/0096048 A1 | 4/2014 | Rottler et al. | |
| 2014/0157165 A1 | 6/2014 | Hoyer et al. | |
| 2015/0005630 A1* | 1/2015 | Jung | A61B 8/565 |
| | | | 600/437 |
| 2015/0134361 A1* | 5/2015 | Molenda | G06Q 10/10 |
| | | | 705/3 |
| 2015/0227501 A1* | 8/2015 | Farjo | G06F 17/241 |
| | | | 715/230 |

\* cited by examiner

DIAGRAM BASED VISUAL PROCEDURE NOTE WRITING TOOL

FIELD

The present application relates generally to computers, and computer applications, and more particularly to computer user interface such as graphical user interface and gesture based interaction, for example, for medical procedure note writing.

BACKGROUND

Vendors currently provide text based procedure note writing, for example, associated with medical examinations. The selection method presented to users such as physicians is based on hierarchical lists of terms. The user is presented with a list of terms relevant to the section he or she is currently writing. The user then selects terms from this list to associate with the exam. In some cases, a user may be presented with new terms that fall under the selected term in a hierarchy. When the user indicates that he or she has selected enough terms the report section is populated with prose describing the selections made by the user.

The method of selection in the existing text based procedure note writing is unnatural and takes a significant amount of user training. For instance, overwhelming amount of options is presented to the procedure note writer and large amounts of actions are required to generate content. The representation of data is dense and relies only on text to show state. The existing text based procedure note writing is not easily adaptable by different devices; for instance, mobile computing devices cannot be used with the currently existing text based method of writing and reviewing procedure notes.

BRIEF SUMMARY

A method and system of providing a diagram based visual procedure note writing is disclosed. The method, in one aspect, may include presenting an image representing a structure on a user interface display. The method may also include presenting a plurality of objects on the user interface display. The method may further include, responsive to an object being placed onto the image of the structure, updating a metadata associated with the object based on a region information associated with a position where the object is placed onto the image, the updated metadata presented on the user interface display. The method may also include composing a note based on the updated metadata.

A diagram based visual procedure note writing user interface system, in one aspect, may include a memory device storing a knowledgebase comprising images and information associated with an anatomical structure. A processor coupled to the memory device may be operable to present an image representing an anatomical structure on a user interface display. The processor may be further operable to present a plurality of objects on the user interface display. Responsive to an object being placed onto the image of the structure, the processor may be further operable to update a metadata associated with the object based the knowledge base and a region information associated with a position where the object is placed onto the image. The processor may be further operable to present the updated metadata on the user interface display. The processor may be also operable to compose a note based on the updated metadata.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

Figure 1:
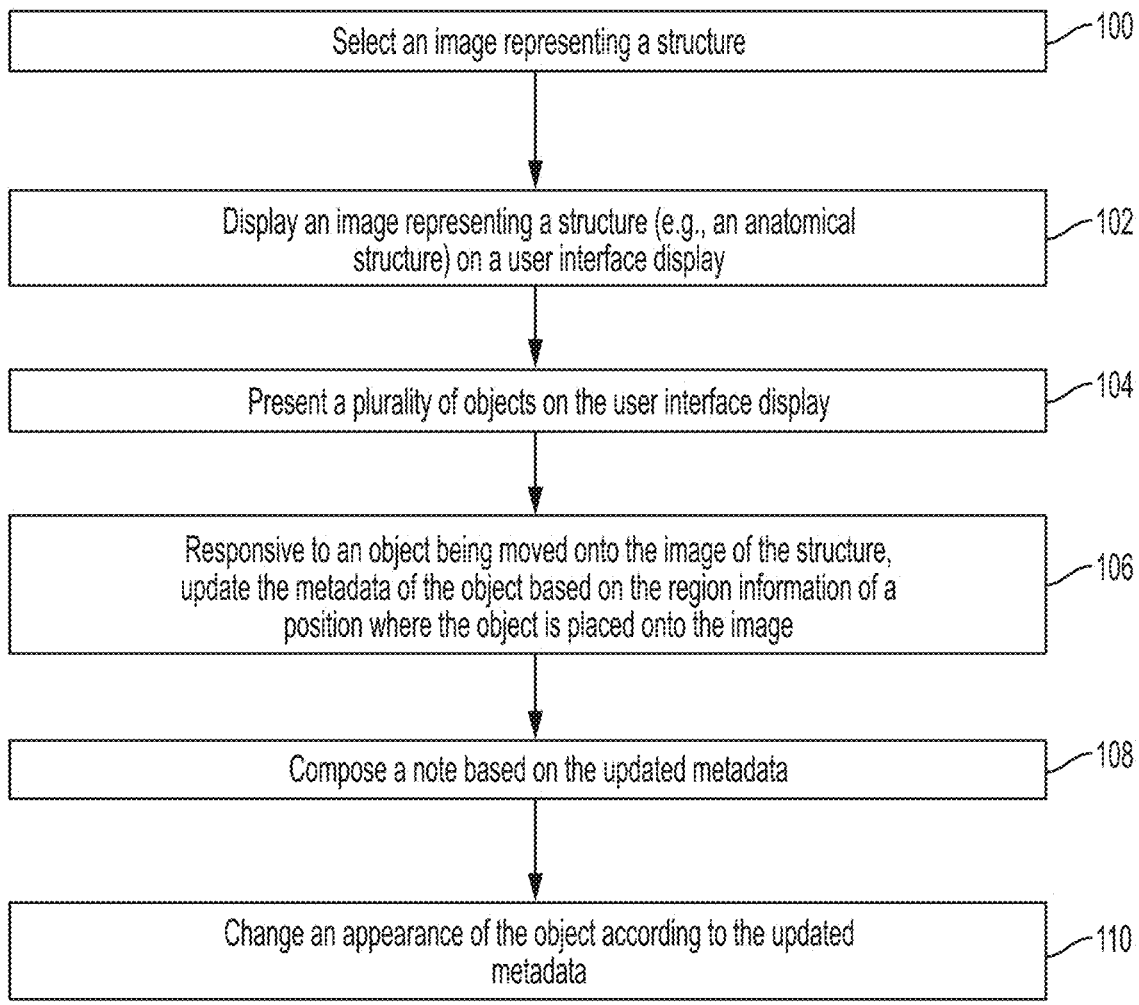
FIG. 1 is a flow diagram illustrating a method of providing a diagram based visual procedure note writing in one embodiment of the present disclosure.

Diagram based visual procedure note writing tool, system and/or methodology are presented. Diagram based visual procedure note writing of the present disclosure in one embodiment incorporates a human computer interface (HCI) technique, for example, a graphical user interface technique that in one aspect provides a natural model for representing findings, for example, medical findings. The interface in one embodiment renders procedure note data easy to understand while requiring minimal interface training. The interface may also reduce the number of necessary user clicks by gathering information implicitly through locations indicated through a diagram, for example, an anatomical diagram. By employing a diagram, the diagram based visual procedure note writing tool in one aspect, increases precision in indicating a finding. In one embodiment, the diagram based visual procedure note writing tool is enabled to be deployed on various devices, for example, on a desktop as a stand-alone application and/or as a server application accessed via a computer network, and mobile devices (e.g., as a mobile application).

A user interface technique of the present disclosure in one embodiment presents a set of diagrams to which one or more terms (also presented via the interface) can be pinned. For instance, the HCI technique of the present disclosure presents a paradigm for describing medical exams by pinning selected terms on a set of diagrams. The HCI technique may be included in a digital medical record system, for example, a graphical user interface of the digital medical record system. For instance, the graphical user interface that implements the HCI technique of the present disclosure may present a diagram of an anatomical structure of a human body shown in a first container, and terms predefined for each pathological lesion shown in a second container in a movable manner. The graphical user interface allows a user (for example, a healthcare professional) to drag and drop the terms onto the diagram to mark a point of interest. Responsive to a term being placed on the diagram, the graphical user interface allows further information (e.g., comment, quantity, diagnosis, picture or the like) to be input to a menu of the term by a specific operation (e.g., double click). In one embodiment, the menu is organized hierarchically, with lower levels of the menu enabled to be hidden and expanded. For example, initially the lower levels of the menu may be hidden, then expanded responsive to a selection made in its upper level. In one embodiment, an appearance (e.g., color, title or the like) of the term is configured to be changed based on a content of the menu. In one embodiment, the diagram contains region information defining what area of the diagram corresponds to a specific part of a structure the diagram is representing. For example, the diagram contains region information defining what area of the diagram corresponds to a specific part of a human organ. When the term is placed on the diagram, the content of the menu of the term (e.g., location) is updated based on the region information.

FIG. 1 is a flow diagram illustrating a method of providing a diagram based visual procedure note writing in one embodiment of the present disclosure. At 100, an image representing a structure is selected. For example, an appropriate image may be selected from a list associated with the type of medical examination being performed. In one embodiment, the image may be preselected based on previous knowledge of the case (e.g., patient's medical condition). For example, if it is known that the patient for whom the image is being displayed does not have any abnormalities in the colon, a clean colon image may be selected automatically. As another example, if it is known that the patient had a hemicolectomy, an image that shows that condition may be selected automatically. The user, for example, a physician, may override the preselected image.

At 102, an image representing a structure is presented on a user interface display. The image includes region information corresponding to an area of the structure. The structure, for example, includes an anatomical structure. The image representing a structure may be presented or displayed in a first container or first area of the user interface display.

At 104, a plurality of objects is presented on the user interface display. The objects may be displayed on a second container or second area of the user interface display. The objects are configured to be movable onto the image of the structure. The objects may be associated with metadata. Metadata shows information about the object.

At 106, responsive to an object being moved onto the image of the structure, the metadata of the object is updated on the basis of the region information of a position where the object is placed onto the image. In one embodiment, the graphical user interface infers information about the object (e.g., finding related to the term) depending on where the object is placed on the diagram. In one embodiment, this may be accomplished by maintaining a map that relates location on the diagram (image) with location of the structure (e.g., organ location). In one embodiment, a knowledgebase that maps the region information with information associated with the object is utilized to update the metadata.

At 108, a note is composed automatically based on the updated metadata, for example, based on the menu items selected by the user. The note writing, for example, uses a sentence modeling technique in conjunction with the metadata items pertaining to the object, to compose a sentence associated with the current finding as specified by the placing of the object on the image and associated metadata, and metadata selection. In one aspect, the change in the appearance of the object is triggered based on location information and an input to the object by a user. The user interface displays or presents the updated metadata associated with the object, e.g., in a pop-up display, as a change in appearance of the object placed on the image, and/or others. At 110, for example, an appearance of the object is changed or updated according to the updated metadata. In the same manner as 110, a change of an appearance of the object placed on the image may be also performed after 106.

Figure 2:
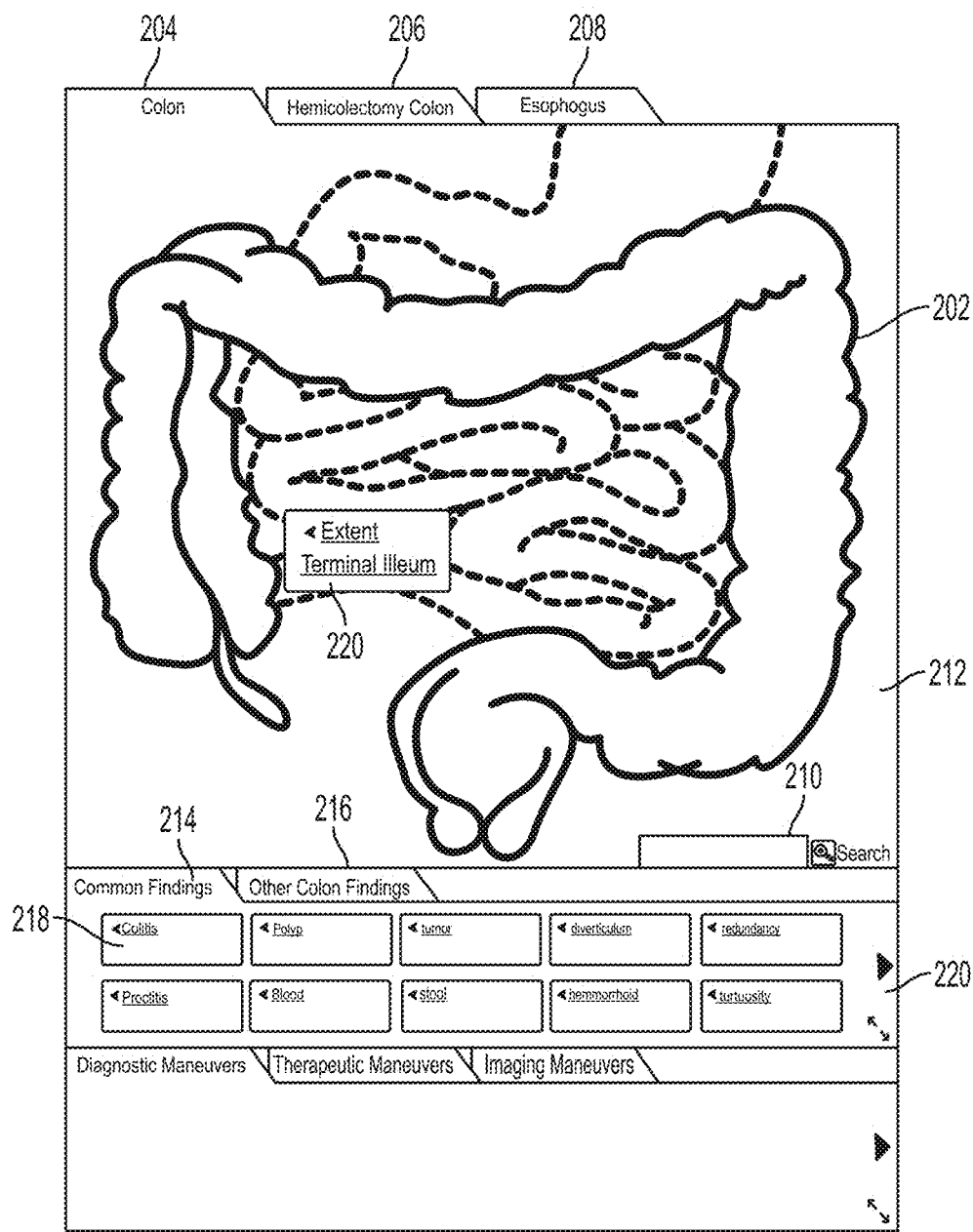
FIG. 2 shows an example image or diagram and objects displayed on a graphical user interface display in one embodiment of the present disclosure.

FIGS. 2-15 show example screen shots that illustrate a graphical user interface (GUI) and techniques of the present disclosure in one embodiment. FIG. 2 shows an example image or diagram and objects displayed on a graphical user interface display in one embodiment of the present disclosure. As shown in FIG. 2, an image 202 of a structure such as an anatomical structure may be displayed in an area of a graphical user interface display. A database of images may be provided, from which the GUI may retrieve and display the images. The image display area of the GUI may display a plurality of tabs (e.g., 204, 206, 208), for instance, each tab for displaying an image of a different structure. A user may select a tab for the desired image to be displayed. The example image display area in FIG. 2 shows tabs for colon, hemicolectomy colon and esophagus. Selecting a tab displays an image associated with the selected tab; in this example, an image of a colon is selected and shown. In one embodiment, an image that represents a structure may be displayed in a first area or first container in the graphical user interface display.

The GUI in one embodiment also presents a set of menus (e.g., 214, 216) that contain terms in a bordered visual container. In one embodiment, each of these terms in the containers (e.g., 218) is drag and drop enabled (and touch and drag enable for mobile devices). The tabs can be selected, and a term or a term in a container is also referred to as an object. In one embodiment, the menus (e.g., 214, 216) are sorted in tabs that the user can scroll through. In the example shown, the menu, "Common Findings" 214 contains terms that fall under the "common finding" menu, e.g., colitis, polyp, tumor, diverticulum, redundancy, proctitis, blood, stool, hemorrhoid, turtuosity, etc., each term in its own container. In one embodiment, the menus (e.g., 214, 216) and the terms contained therein are retrieved from a database that stores attributes related to the selected image. In one embodiment, the set of menus that contain terms in a visual container are displayed in a second area (e.g., 220) of the graphical user interface display.

The GUI in one embodiment of the present disclosure also may allow a user to search for term 218, for instance, by providing a search field or box 210. Responsive to the user inputting a search term, the GUI may search for and retrieve a matching term in a container (e.g., 218). Typing a term in the search box 210 may present that term in a container, for example, under one or more of the menus (e.g., 214, 216). For instance, the term is searched for in the database that stores attributes related to the selected image, and responsive to finding the term, the term in a visual container may be displayed in a menu area (e.g., 214, 216).

Figure 3:
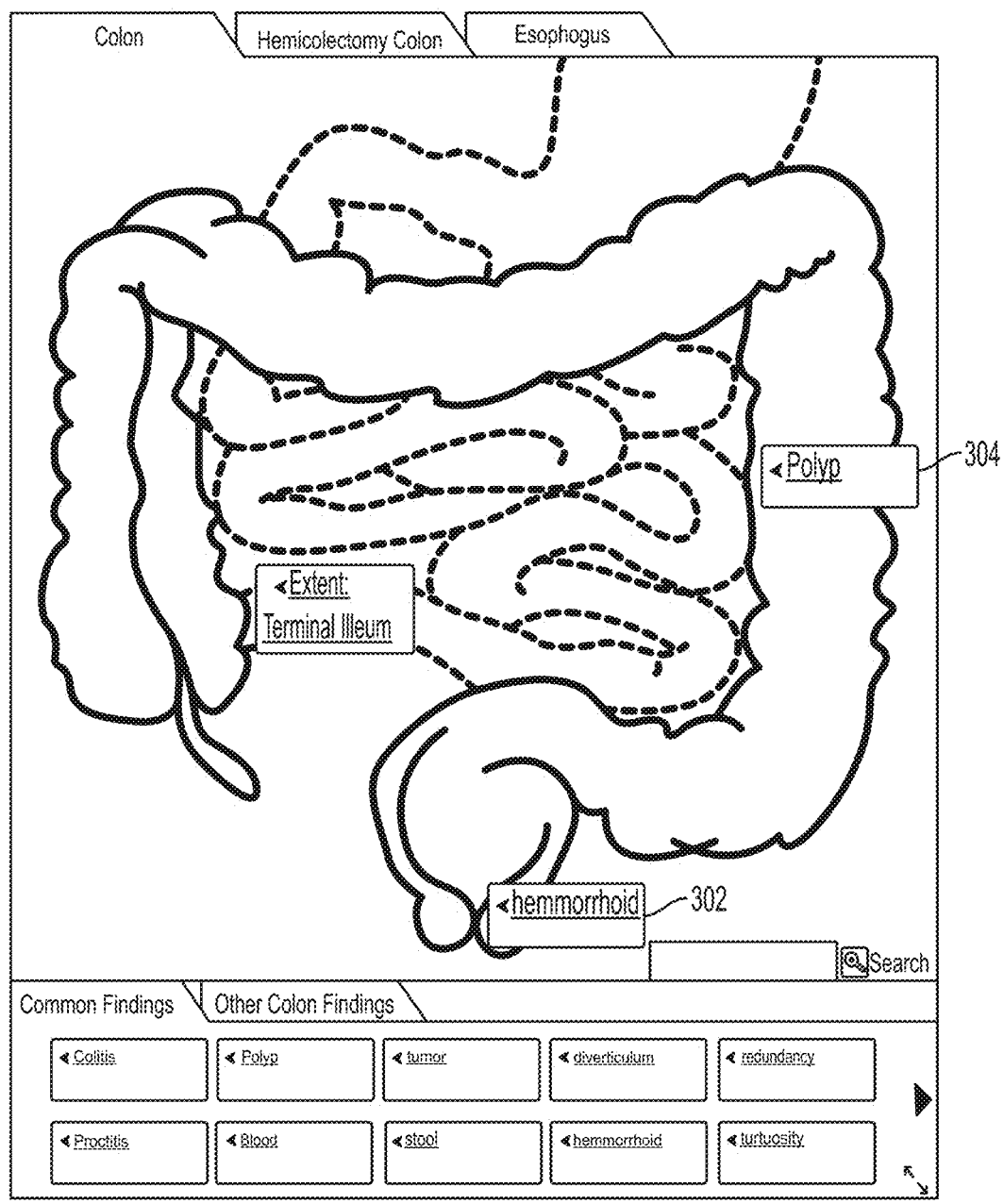
FIG. 3 shows an example graphical user interface display having objects placed on an image in one embodiment of the present disclosure.

One or more of the terms or objects (e.g., 218) may be placed on the image (e.g., 202). For example, the user interface allows users to transpose or move (e.g., drag and drop, gesture, or touch and drag) terms onto the anatomical diagram (e.g., 202). This allows the user (e.g., a physician) to mark with high precision the location of the action or finding associated with the term. FIG. 3 shows an example screen with the terms (or objects) moved onto the image. In this example, the user dragged "hemorrhoid" object 302 to an area in the anus portion of the image, and "polyp" object 304 to an area in the descending colon portion of the image. The same term can be moved onto different portions of the image, e.g., by dragging the term from the menu area and dropping it on an area of the image, then again by dragging the term from the menu area and dropping it on another area of the image.

In one embodiment, an image that is displayed may already have a term or an object placed on the image. For instance, an image template may be pre-populated with selections, for example, selected one or more objects placed on it, making them standard selections for anyone using that template. For example, in FIG. 2, the image is displayed with the Extent tag (term or object) 220 already placed on the terminal ileum portion of the image.

Figure 4:
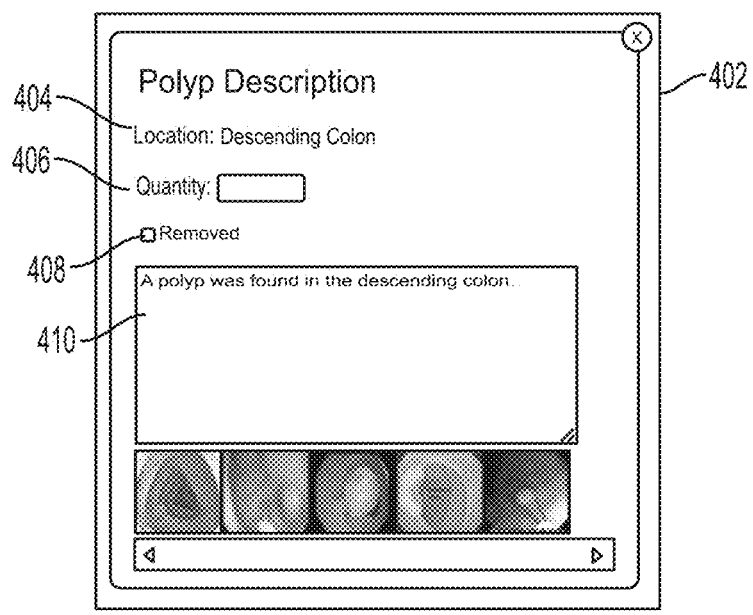
FIG. 4 shows an example metadata of an object, for example, term description context that is displayed with associated menus in one embodiment of the present disclosure.

In one embodiment, terms can be further described by changing the context to focus on that specific finding. For example, selecting the term from where it is placed on the image (e.g., by double clicking (or by another gesture) the polyp object 304 in FIG. 3) brings up the polyp description context and shows or displays the related menus. FIG. 4 is an example context that is displayed with associated menus in one embodiment of the present disclosure. In this example, the polyp description context 402 is changed according to the location where the polyp object is placed in the image, in this example, the descending colon. For instance, the menu items (also referred to as menus) that are displayed in the polyp description context 402 are related to polyp in its current location, descending colon. The menu items in this example include the location 404, quantity 406, and removed 408. In one embodiment, the menus within context of a term are organized hierarchically, with lower levels of menus hidden unless a selection is made in a menu above it in hierarchy. For example, if a user selects "Removed", then the menus for removal techniques are shown. The description context 402 also may include a section that shows the note 410, e.g., sentences as generated according to the menu items.

Figure 5:
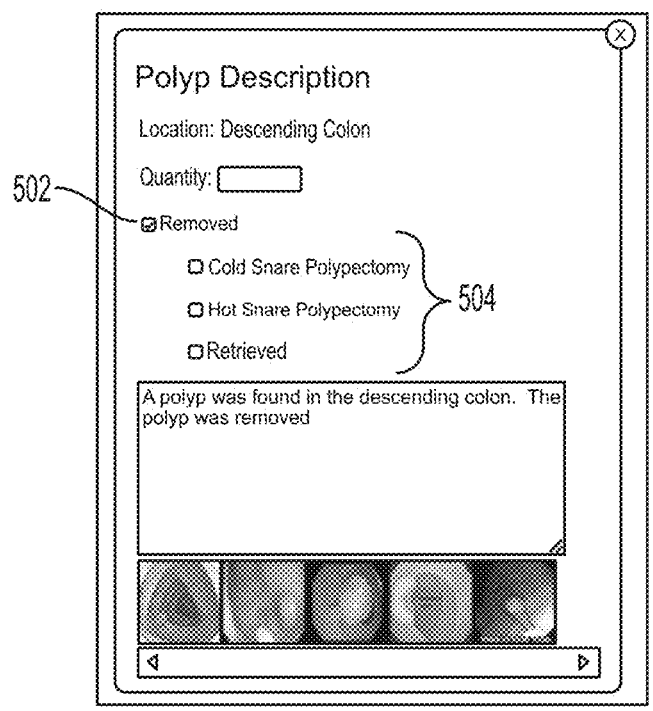
FIG. 5 shows an example of a term description context with expanded menu items in one embodiment of the present disclosure.
Figure 6:
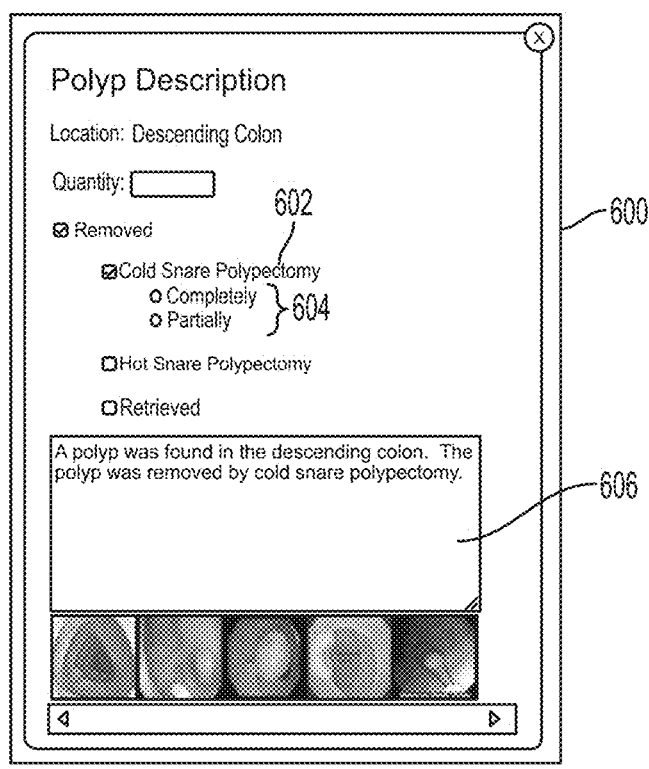
FIG. 6 shows an example of a term description context with further expanded menus in one embodiment of the present disclosure.

FIG. 5 shows an example of a term description context with expanded menu items in one embodiment of the present disclosure. Responsive to the "Remove" option being checked (shown at 502), "Cold Snare Polypectomy", "Hot Snare Polypectomy" and "Retrieved" options become available as shown at 504. FIG. 6 shows an example of a term description context with further expanded menus in one embodiment of the present disclosure. For example, responsive to a user selecting "Cold Snare Polypectomy" menu item 602, more options become available as shown at 604.

In one embodiment, the GUI of the present disclosure in one embodiment dynamically in real time generates and presents a sentence (as note writing), e.g., responsive to a user selecting a menu item in the term description context. For instance, with each selection made on the context menu the effect of the selection is shown immediately in the sentences 606 being generated to describe the finding. In one aspect, the GUI focuses on the context of one term to generate sentences in real time, e.g., as the terms are selected, rather than having to generate sentences for the entire section all at the same time.

Figure 7:
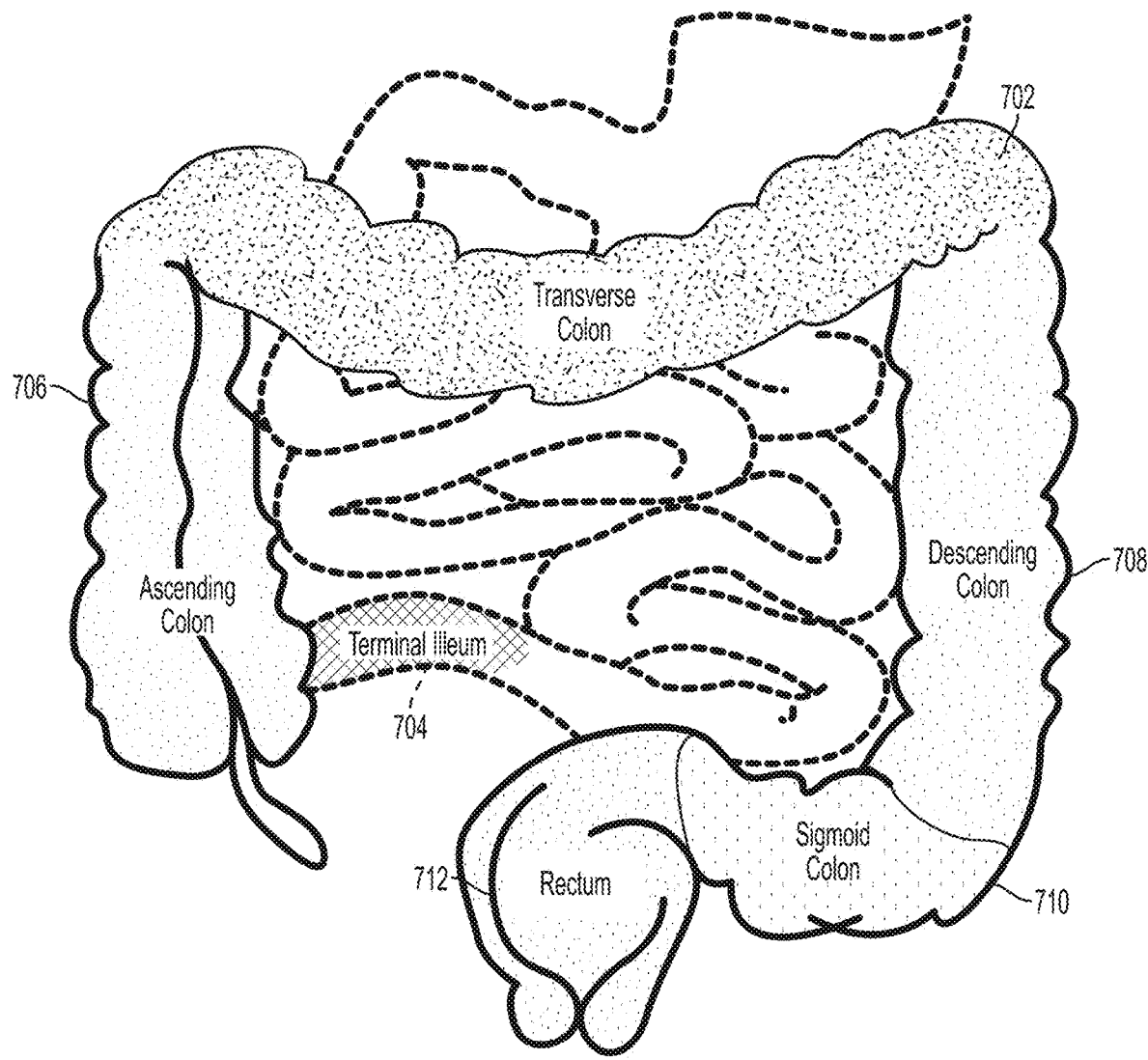
FIG. 7 shows an example diagram that illustrates a possible pairing of diagram areas and organ locations.

As described above, the GUI infers information about the finding depending on where it is placed on the diagram. In one embodiment, a map relating location on the diagram with structure location (e.g., anatomical structure such as organ location) is stored and maintained (e.g., in a database). FIG. 7 shows an example diagram that illustrates a possible pairing of diagram areas and organ locations. For example, if an object is placed in the area outlined at 702, the object is then marked as being in the transverse colon. If the object is placed in the area at 704, it is marked as being part of the terminal ileum. Similarly, if the object is placed in the area at 706, it is marked as being part of the ascending colon. If the object is placed in the area at 708, it is marked as being part of the descending colon. If the object is placed in the area at 710, it is marked as being part of the sigmoid colon. If the object is placed in the area at 712, it is marked as being part of the rectum.

Figure 8:
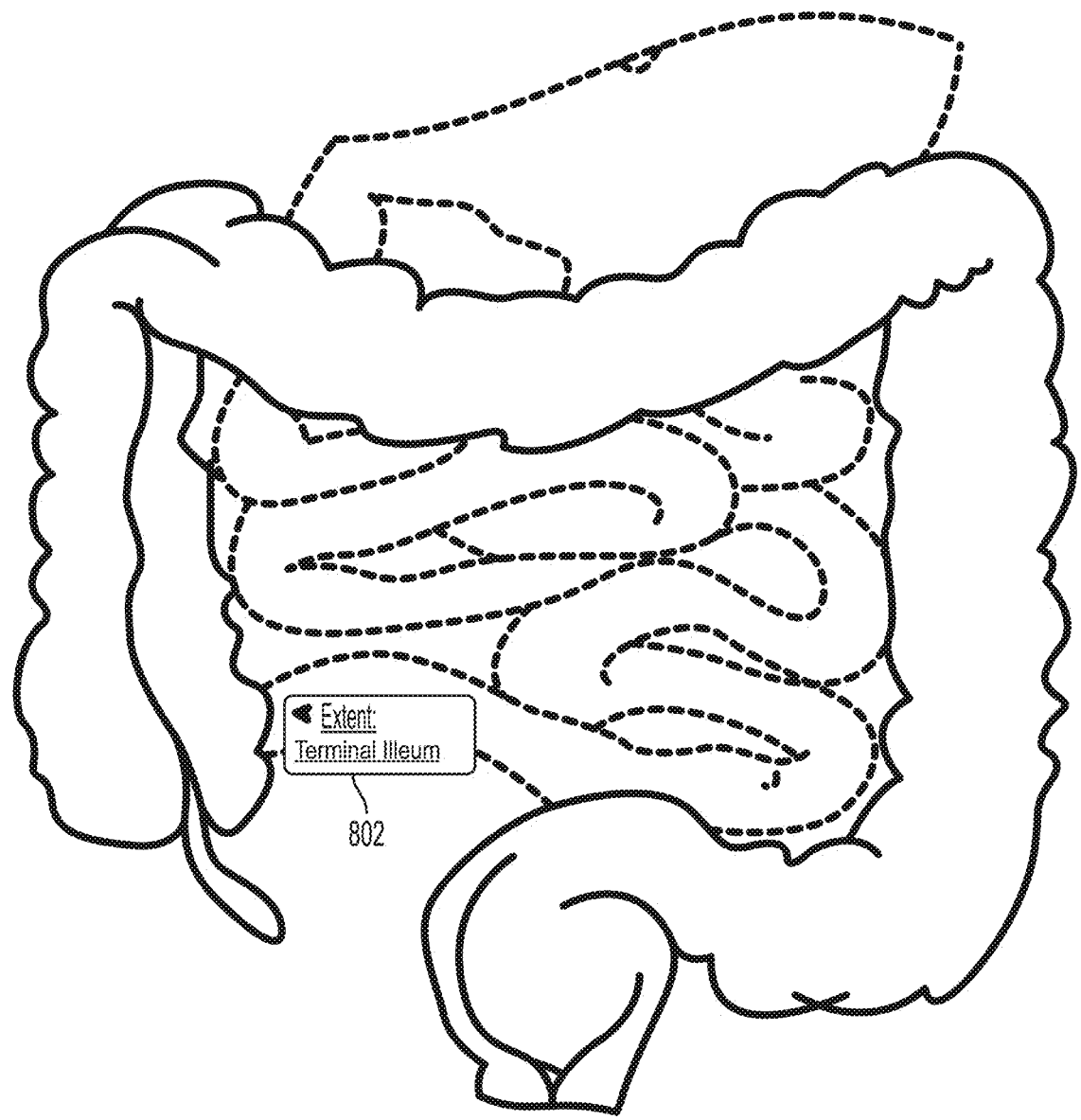
FIG. 8 shows an example diagram with the organ location information attached to the object.

Based on the placement of the object (term), metadata associated with the term is updated. For example, the structure location information (e.g., the organ location information) is attached to the object (term). FIG. 8 shows an example diagram with the organ location information attached to the object. For example, the "Extent" object placed in the terminal ileum area includes updated location information as shown at 802. Metadata refers to data about objects or terms in the present disclosure. Examples of metadata may include, but are not limited to structure location information, quantity, a type of a medical procedure performed (e.g., whether removed), and notes, which describe an object or term. In addition to the location information and predetermined labels associated with the location information, metadata may also include information about an object or term that a user inputs (e.g., actual quantity (e.g, 5)), check mark of on a menu item that indicates a type of medical procedure performed (e.g., removed or another procedure).

Figure 9:
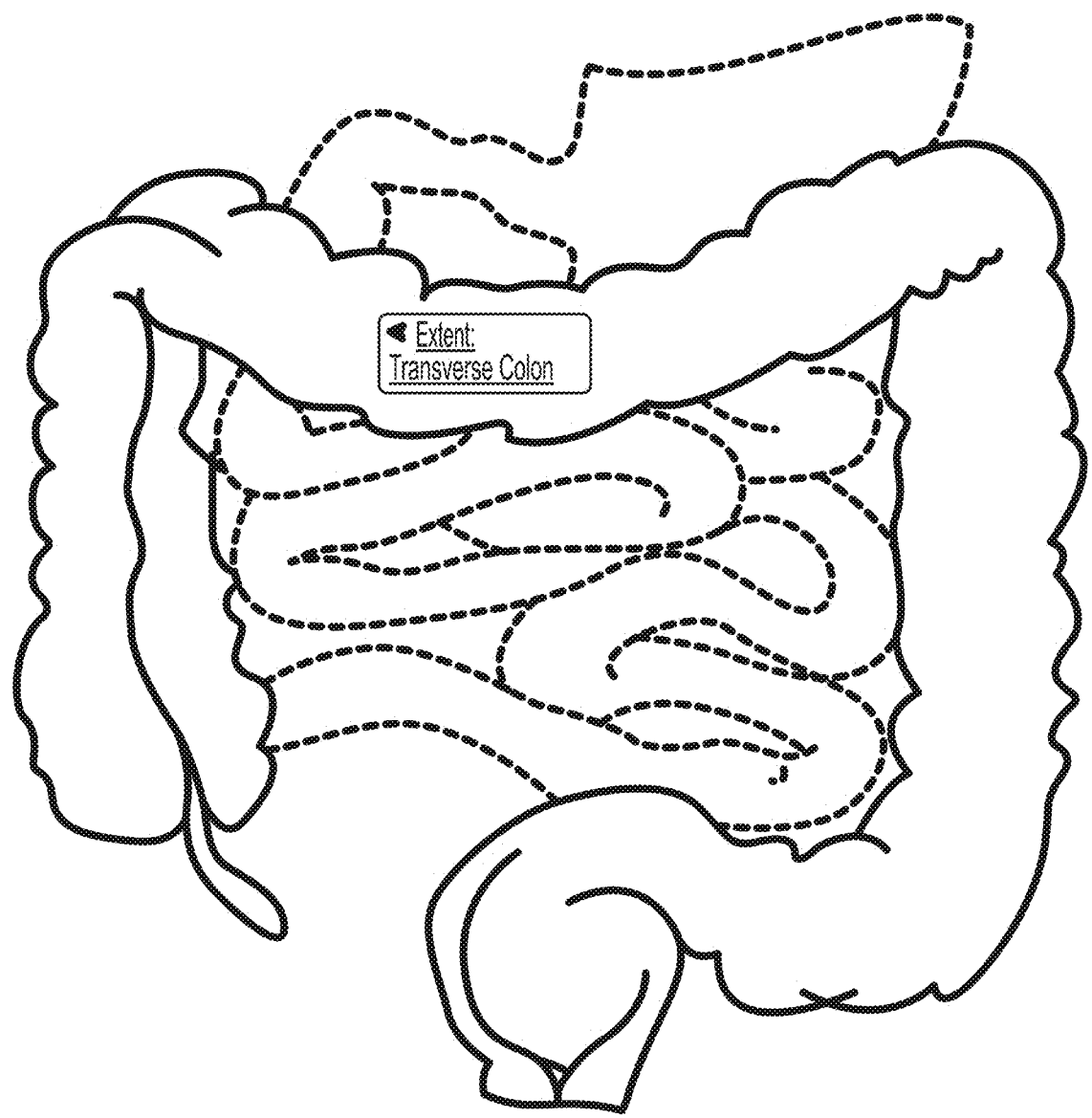
FIG. 9 shows an example diagram with an "extent" object placed in a section of an image.
Figure 10:
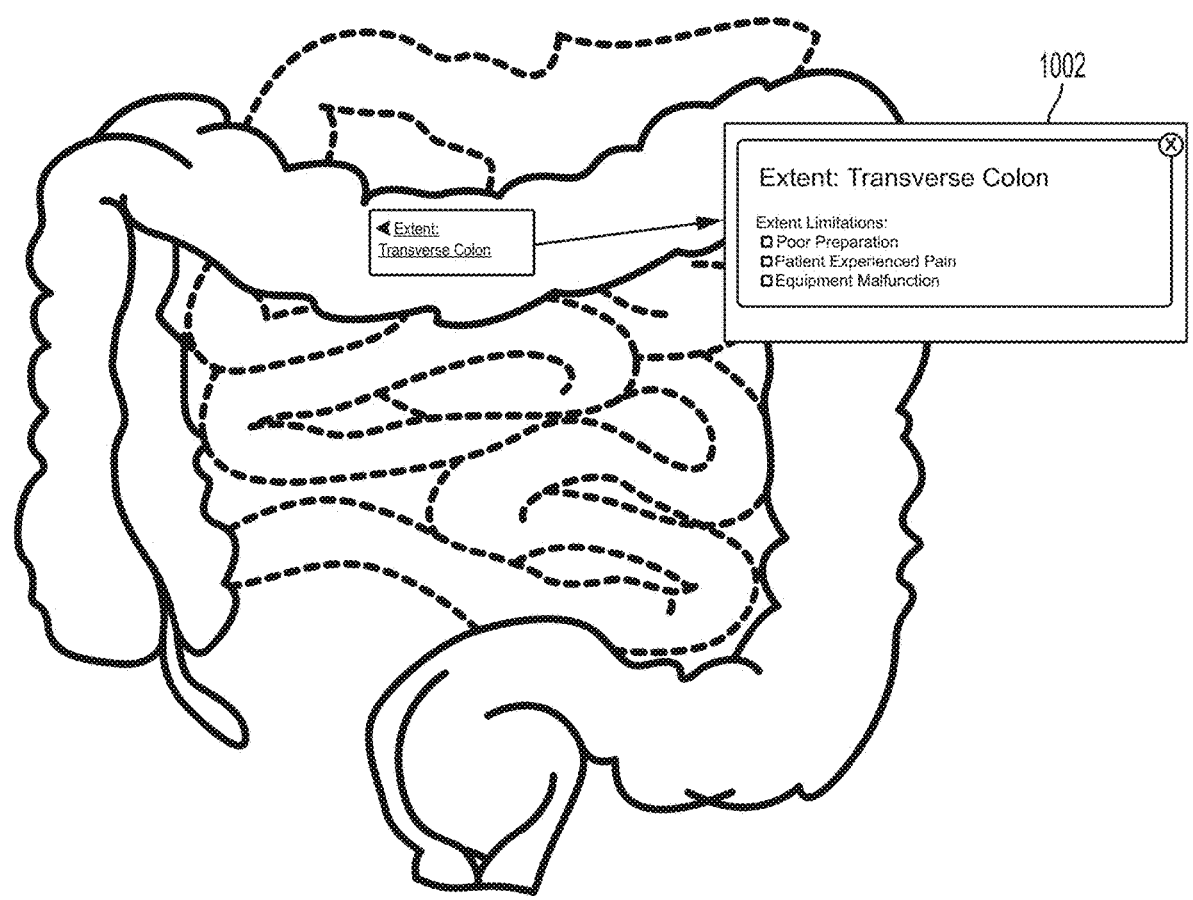
FIG. 10 shows an example diagram showing metadata, e.g., menus as related to an object placed in a section of an image.

Another example of metadata associated with the term that is updated based on the placement of the object includes the menus related to the term. For instance, the menus (or menu items) displayed when a term is brought into context are also adjusted to the appropriate menus for the placement of the term. For example, when an "extent" object is placed in the transverse colon, the appropriate menus to display might relate to the limitations of extent as related to the transverse colon. FIG. 9 shows an example diagram with an "extent" object placed in the transverse colon. FIG. 10 shows an example diagram showing the menus 1002 as related to the "extent" object in the transverse colon area.

Figure 11:
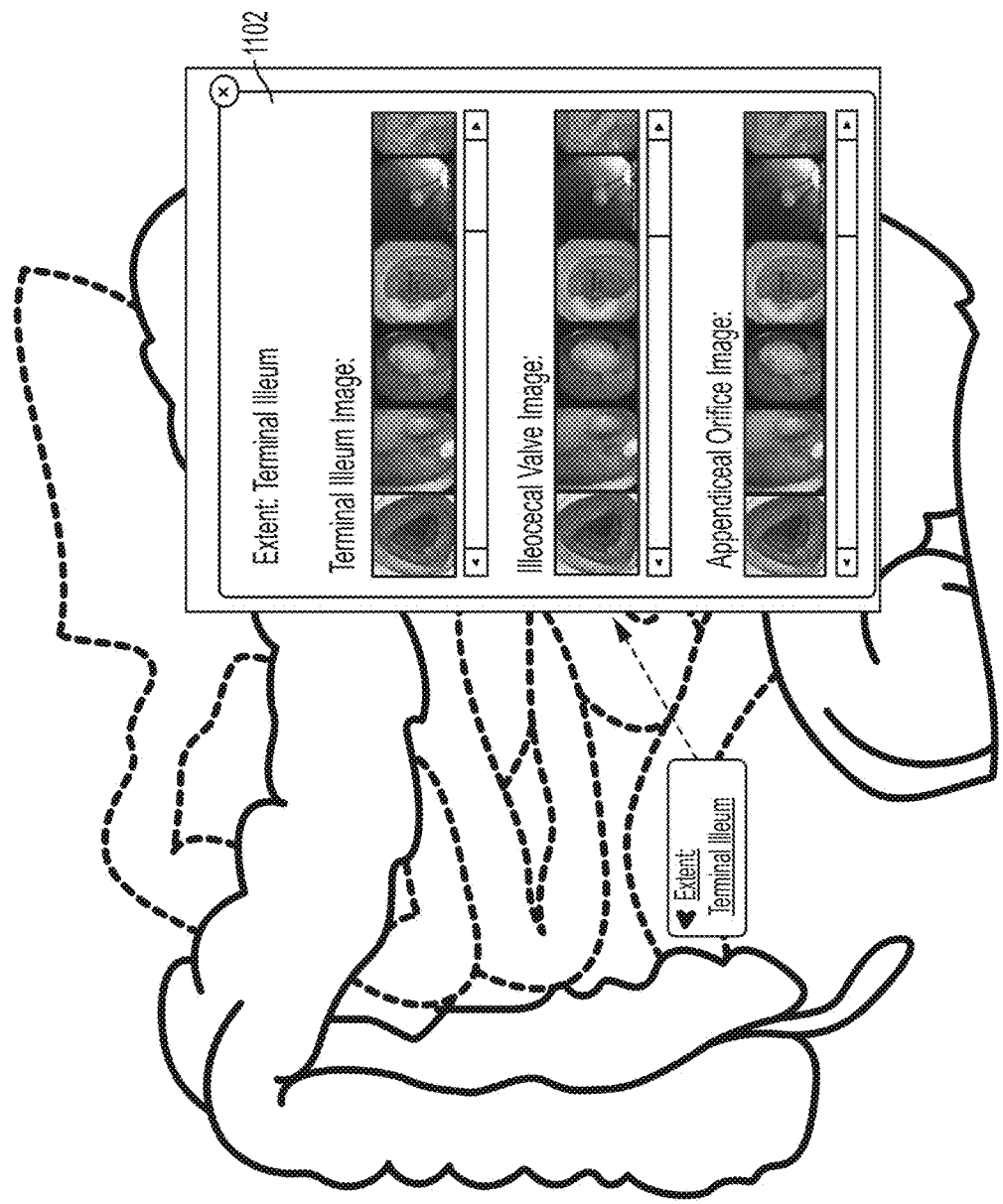
FIG. 11 shows an example of metadata and description options that are updated as a result of placing an object in a different section or location of an image in one embodiment of the present disclosure.

As another example, if the "extent" object or term is placed on the terminal ileum, the menus that are relevant to the extent finding change from extent limitation explanations (as related to the transverse colon as shown in FIG. 10 at 1002) to another, e.g., landmark photography. FIG. 11 shows the menus changed to photography 1102 as related to the "extent" object in the terminal ileum area. For example, the GUI may present a photography related to an object of a structure for additional user input. For instance, the GUI presents a photography 1102 for user input to indicate which images relate to the extent. In one embodiment, the user is shown all the images that were taken, and is asked to select the ones that correspond to landmarks associated with extent. The user inputs or indicates which one or more of the shown images are related to the extent. For example, a user can designate one or more images on photography 1102. The one or more images designated by a user are associated with the object as the most relevant image(s), for instance, as the object's metadata.

Figure 12:
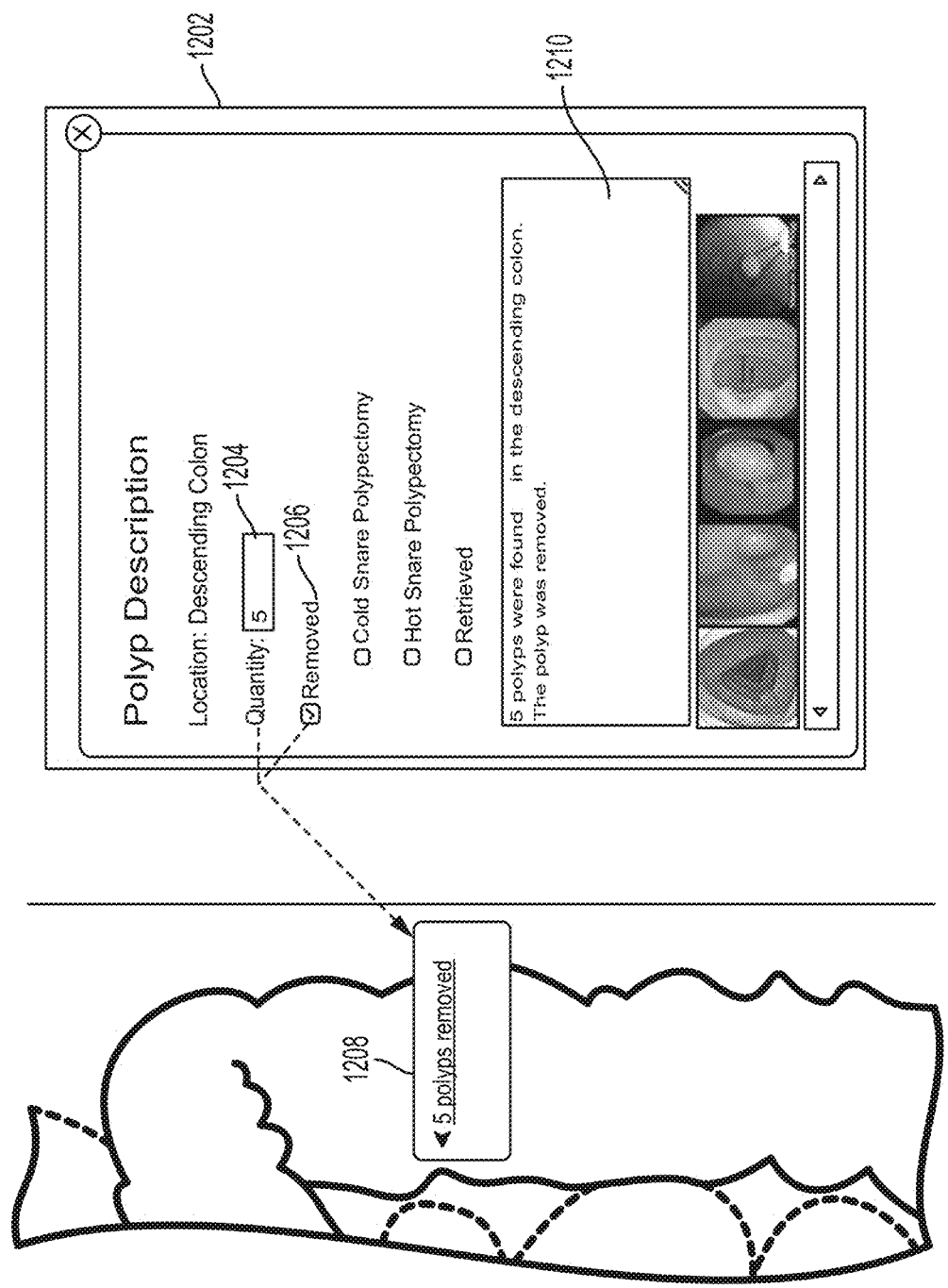
FIG. 12 shows an example of detailed display on a diagram in one embodiment of the present disclosure.

In one embodiment, details may be displayed from in context menus on the diagram. FIG. 12 shows an example of detailed display on an anatomical diagram. For instance, an inputting or selecting an item of the graphical user interface may change the appearance of the object, for instance, to convey more detail or more information. The details that are presented or displayed may be defined in a knowledgebase from which the GUI draws the detailed content. For instance, the object or term's title may change on the diagram. FIG. 12 shows an example anatomical diagram with the "polyp" object placed on the descending colon diagram. Responsive to an input in the quantity menu 1204 and selection of the "removed" menu 1206 in the polyp description context 1202, the "polyp" object's title changes to "5 polyps removed" on the diagram as shown at 1208. Generally, selections on menus may append text to the title of the term placed on a diagram. In one embodiment, the note that is composed is also updated in real time dynamically according to the input and selection as shown at 1210.

Figure 13:
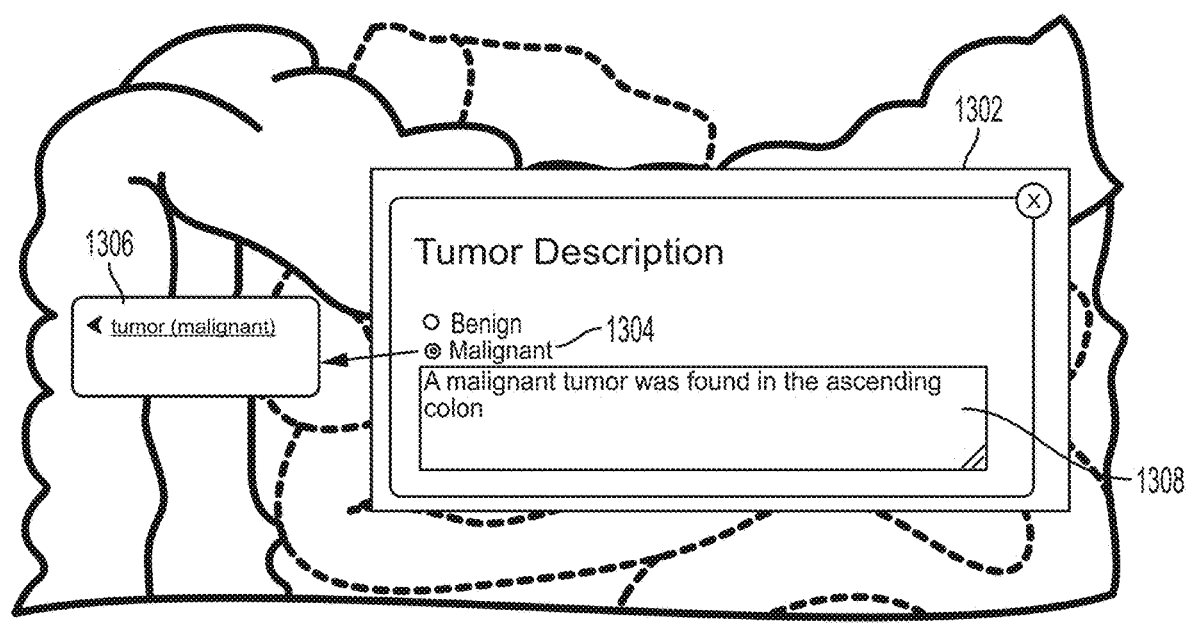
FIG. 13 shows another example of changing the appearance of the object on the diagram in one embodiment of the present disclosure.

FIG. 13 shows another example of changing the appearance of the object on the diagram in one embodiment of the present disclosure. In this example, a selection on the context menu 1304 from the tumor description context 1302 changes the color of the "tumor" object or term's container 1306. This example also shows the note 1308 that is composed automatically in real time based on the current selection.

Figure 14:
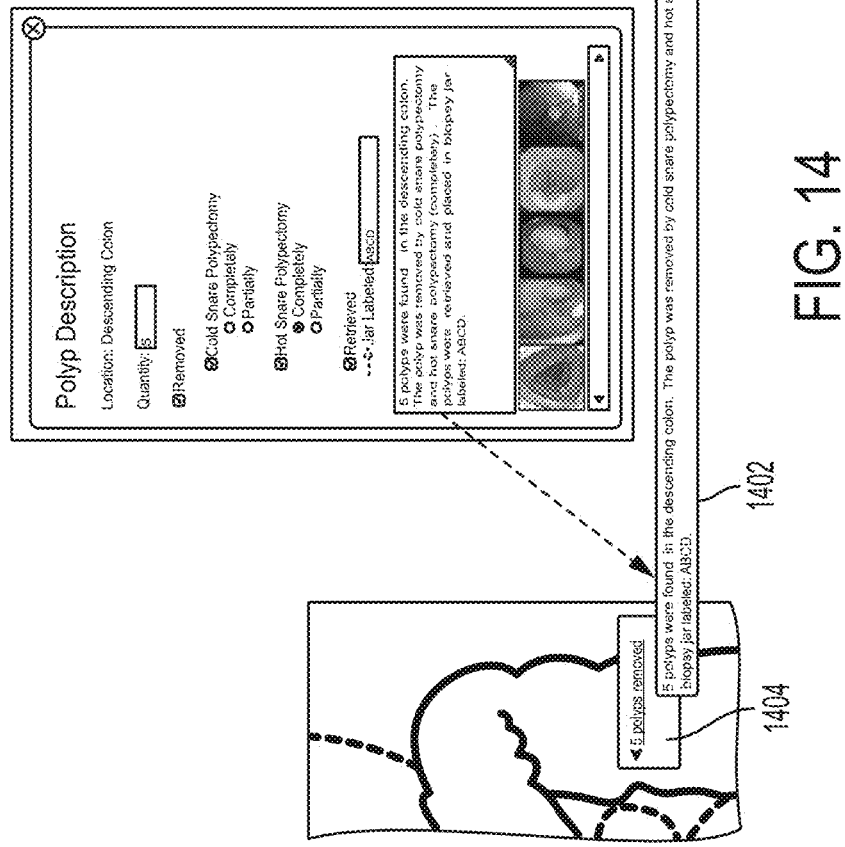
FIG. 14 shows an example user interface display, in which the text of a sentence is made visible on hover over on an object in one embodiment of the present disclosure.
Figure 15:
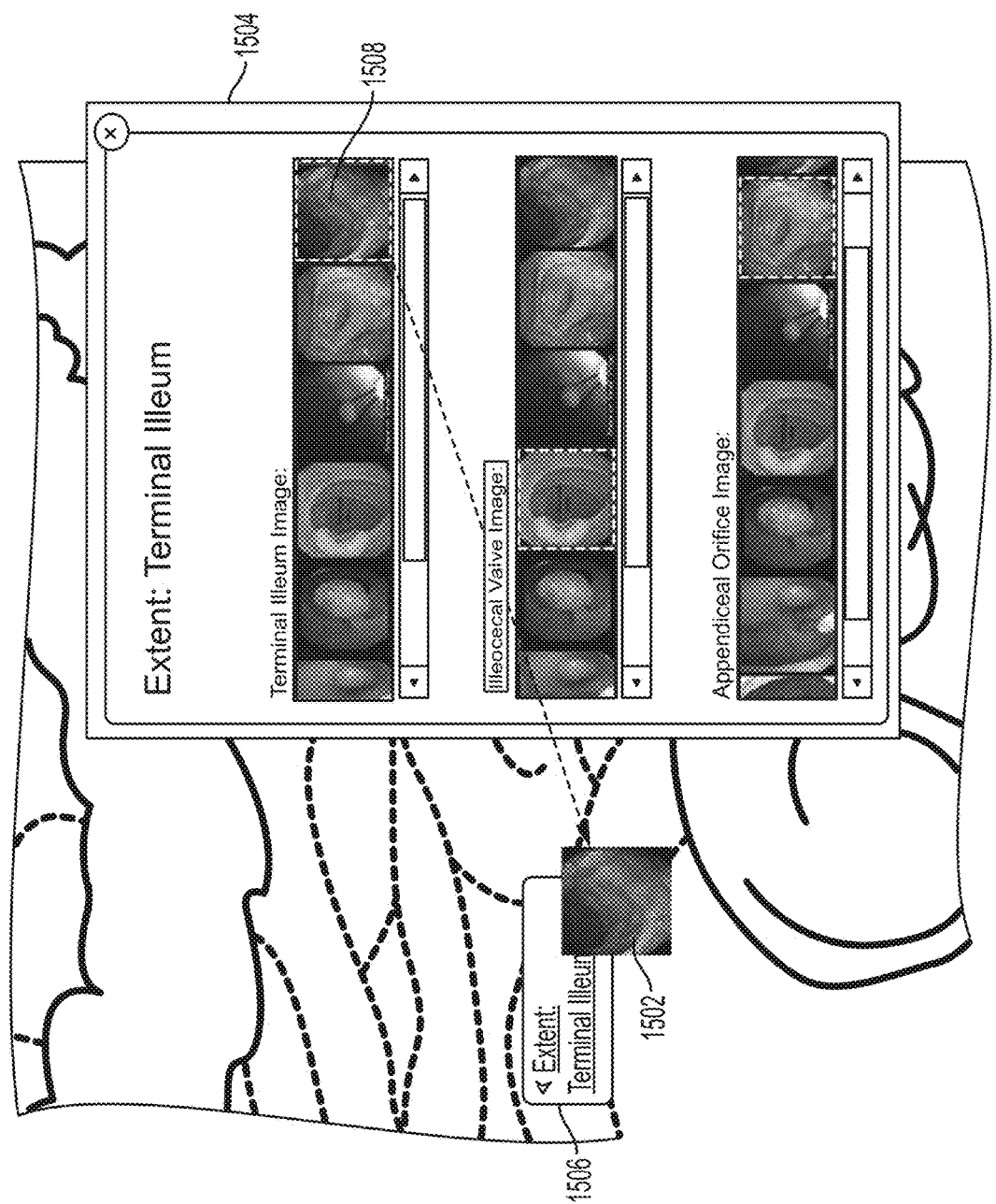
FIG. 15 shows another example user interface display, in which an image is displayed on hover over in one embodiment of the present disclosure.

In one embodiment, gestures such as a hover over on the object or the object's container may render detailed information visible on the diagram, e.g., adjacent to the object. FIG. 14 shows an example, in which the text of the sentence 1402 is made visible on hover over on the "polyp" object 1404. FIG. 15 shows another example, in which an image is displayed on hover over. For instance, the image 1502 from an "extent" object's description context 1504, for instance, determined to the most relevant image 1508, is displayed on hover over on the "extent" object 1506 placed on the diagram. The most relevant image 1508, for example, may have been determined based on user input as described with reference to FIG. 11 above. In another aspect, the most relevant image 1508 may be determined automatically. For example, a complete examination of the colon may have been performed, during which all parts of the colon were visible (or at least reached), and the images of the parts taken. The image that is most relevant to terminal ileum object may be the furthest down the colon. For example, the order of distance may be defined as follows: appendeceal orifice, ileocecal valve, then terminal ileum. If a user reaches terminal ileum then it is implied that the user reached the previous two locations, and therefore, the terminal ileum is determined to be "the most relevant". The above method describes one example of how "relevance" is recorded programmatically. As another example, a value may be associated with each type of metadata, and the most relevant image is the metadata with the highest value (in the above case, appendecial orifice=1, illeocecal valve=2, then terminal ileum=3). Yet in another aspect, a flag such as an "important" flag may be defined, which may be set to true or false. In this case, any "important" data is shown in the title.

Figure 16:
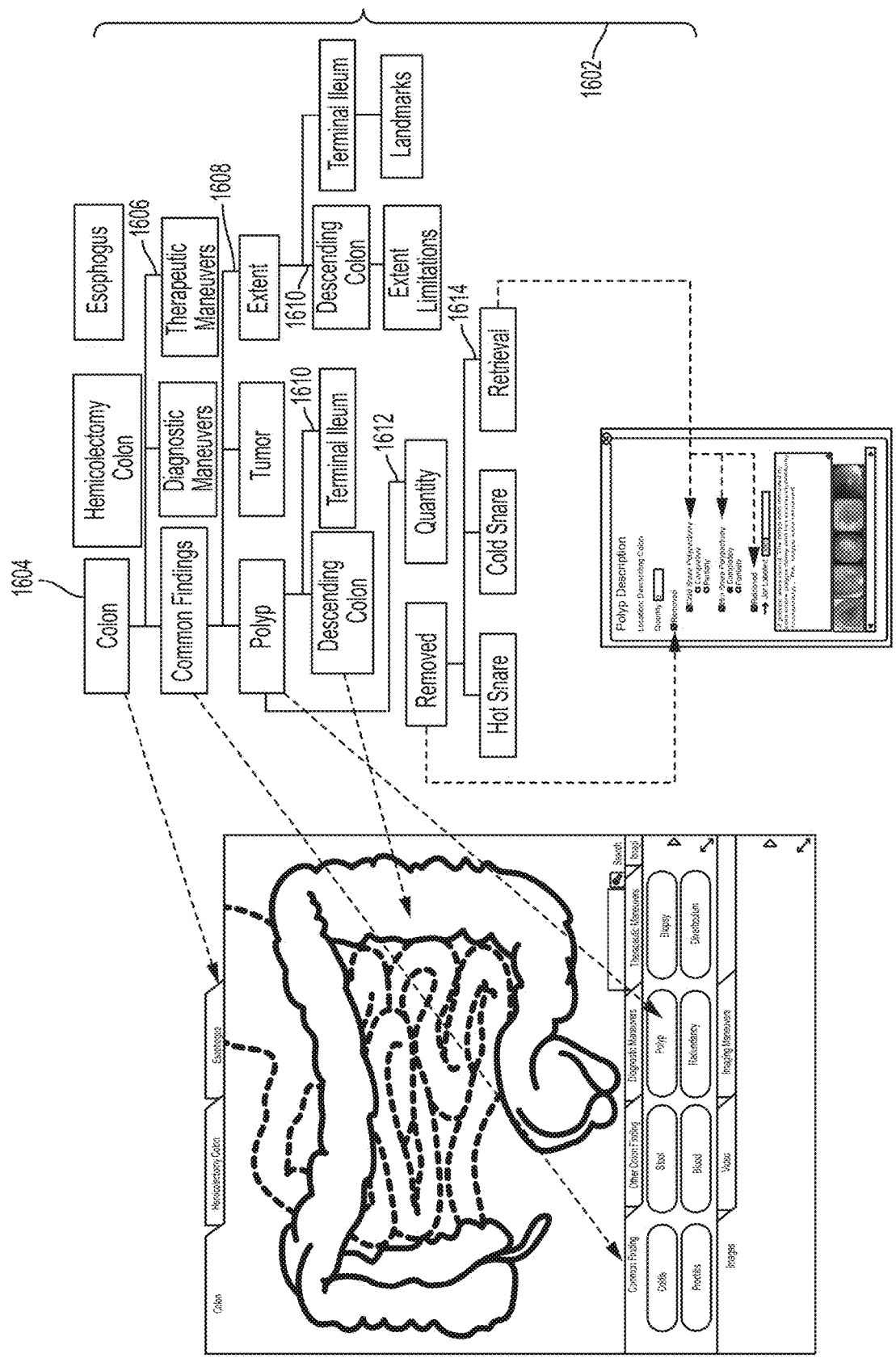
FIG. 16 illustrates an underlying structure of a knowledgebase (KB) from which the GUI can be rendered in one embodiment of the present disclosure.

FIG. 16 illustrates an underlying structure of a knowledgebase (KB) from which the GUI obtains the data and populates the user interface display in one embodiment of the present disclosure. In one aspect, the GUI structure in the present disclosure allows details to be populated from existing knowledgebase. In one embodiment, a knowledgebase 1602 is structured or organized so that it follows a uniform layout, grouping terms together by level logically for the use of the GUI. Each level of the KB relates to a set of elements on the GUI. For example, a level (e.g., the first level) 1604 of the KB structure for the section is reserved for different structures (and respective images or diagrams), for example, different organs (and respectively different anatomical diagrams). Another level under the structure level (e.g., the second level) 1606 shows the tabs organizing the terms. Yet another level (e.g., the third level) 1608 shows the actual terms that can be moved. In one embodiment, this level 1608 contains the first instance of sentence models. Still another level (e.g., the fourth level) 1610 maintains information about the location within the organ. Further another level, (e.g., the fifth level) 1612 maintains the first level of details that a user can input in context, and any lower level 1614 maintains any further detail below that hierarchically. This normalized structure allows for sentences to be generated using existing KB sentence models algorithms. For example, sentences may be composed as part of the note, by using existing sentence models and selected menu items pertaining to the object in the KB hierarchy.

Figure 17:
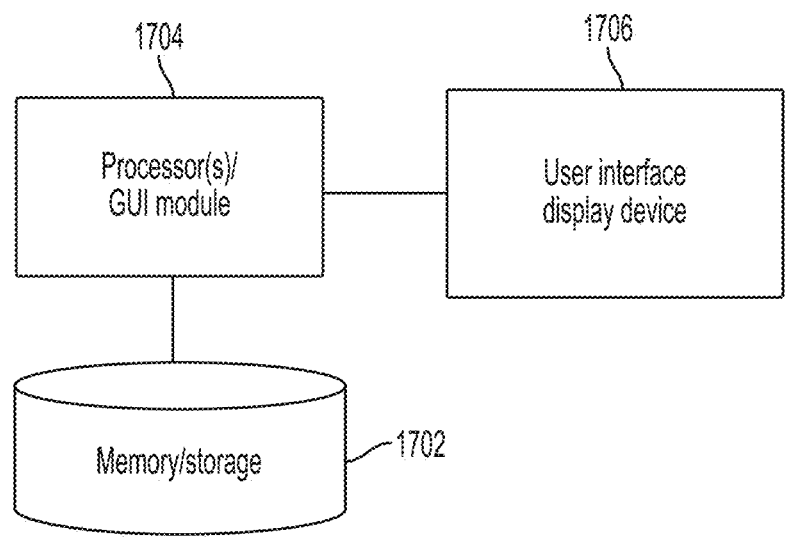
FIG. 17 is a diagram showing components of a system of the present disclosure in one embodiment.

FIG. 17 illustrates components of a diagram based visual procedure note writing system in one embodiment of the present disclosure. A storage or memory device may store a knowledgebase 1702, e.g., as described above and shown in FIG. 16. The knowledgebase 1702 may include images of structures (e.g., anatomical structures) and information associated with the structures. As described above, the knowledgebase 1702 may store the information in a hierarchical manner, for example, a hierarchical tree data structure. One or more processors 1704 may perform the HCI or GUI functionalities described above. For example, a processor 1704 presents an image representing a structure (e.g., an anatomical structure) retrieved from the knowledgebase 1702 on a user interface display 1706, e.g., in a first area of the user interface display. The processor 1704 also presents a plurality of objects on the user interface display 1706, e.g., in a second area of the user interface display. The plurality of objects is defined under a level that represents the displayed image in the knowledgebase. Responsive to an object being placed onto the image of the structure, the processor 1704 updates metadata associated with the object based on the information defined in the knowledge base 1702 and region information associated with a position where the object is placed onto the image. The region information, for example, is determined based on a map relating location on the image with the structure information (e.g., anatomical organ information). The processor 1704 may present the updated metadata on the user interface display 1706 and compose a note based on the updated metadata. The note as composed is presented on the user interface display 1706, e.g., in real time. In one aspect, the processor 1704 may change an appearance of the object on the user interface display 1706 according to the updated metadata. As described above, the updated metadata may include description and menus associated with the object in context with the position of the object on the image, and the processor may compose the note in real time responsive to receiving an input associated with the menus. Also as described above, the processor 1704 may render detailed information visible on the user interface display responsive to detecting a hover over on the object placed on the image.

The GUI techniques described above may be implemented using computer languages such as HTML5 and JavaScript, but not limited to those languages. In one aspect, the functionalities and modules of the system and methods of the present disclosure may be implemented or carried out distributedly on different processing systems or on any single platform, for instance, accessing data stored locally or distributedly on a computer network.

Various aspects of the present disclosure may be embodied as a program, software, or computer instructions embodied or stored in a computer or machine usable, readable or executable medium, which causes the computer or machine to perform the steps of the method when executed on the computer, processor, and/or machine. For instance, a program storage device readable by a machine, tangibly embodying a program of instructions executable by the machine to perform various functionalities and methods described in the present disclosure may be provided.

The system and method of the present disclosure may be implemented and run on a general-purpose computer or special-purpose computer system (or device). The computer system may be any type of known or will be known systems and may include a hardware processor, memory device, a storage device, input/output devices, internal buses, and/or a communications interface for communicating with other computer systems in conjunction with communication hardware and software, etc. The GUI techniques of the present disclosure may also be implemented on a mobile device or the like.

Figure 18:
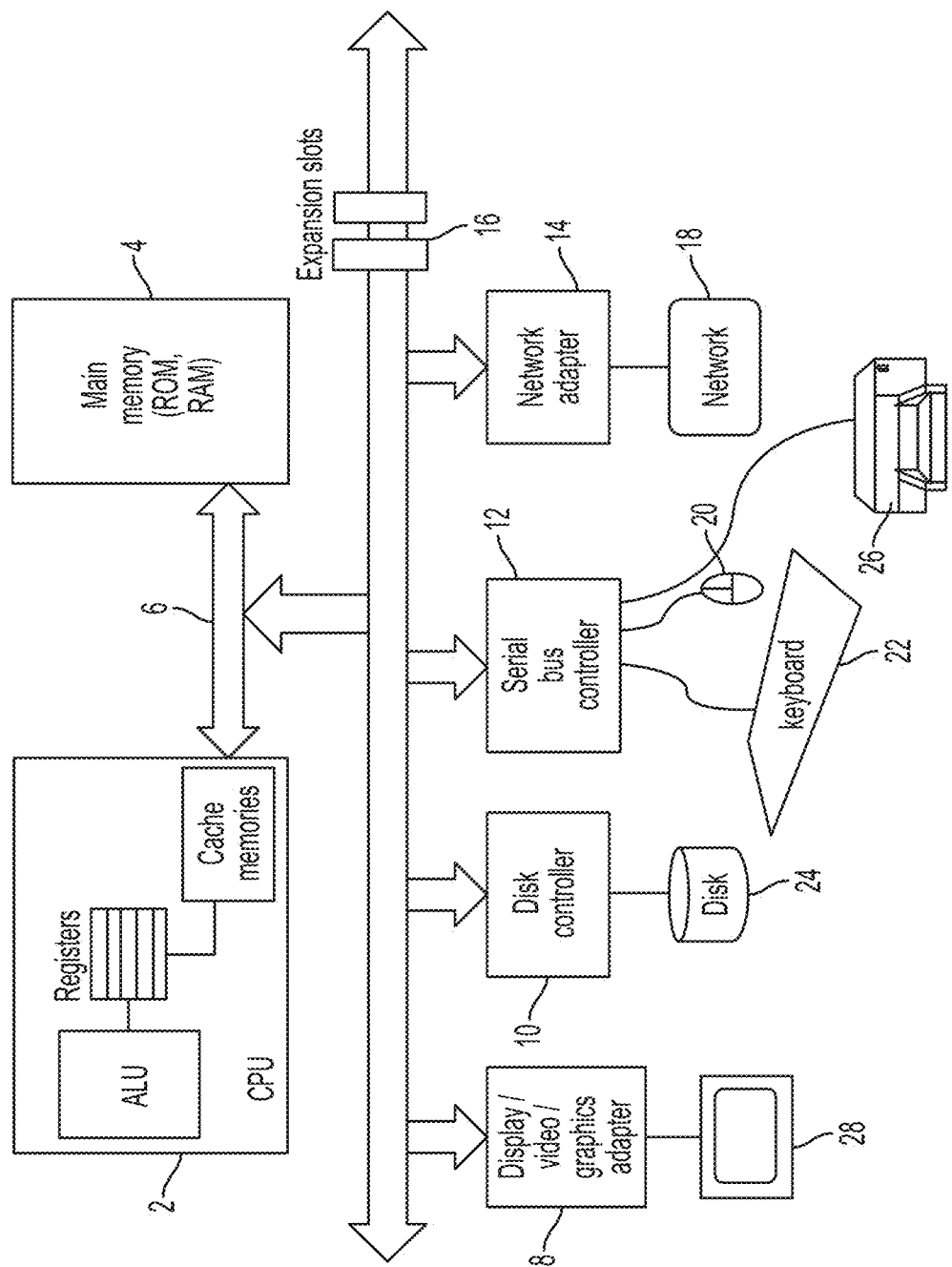
FIG. 18 illustrates a schematic of an example computer or processing system/device that may implement a system in one embodiment of the present disclosure.

FIG. 18 illustrates an example computer system that may implement the system and/or method of the present disclosure. One or more central processing units (e.g., CPUs) 2 may include one or more arithmetic/logic unit (ALU), fast cache memory and registers and/or register file. Registers are small storage devices; register file may be a set of multiple registers. Caches are fast storage memory devices, for example, comprising static random access (SRAM) chips. Caches serve as temporary staging area to hold data that the CPU 2 uses. Shown is a simplified hardware configuration. CPU 2 may include other combination circuits and storage devices. One or more central processing units (CPUs) 2 execute instructions stored in memory 4, for example, transferred to registers in the CPU 2. Buses 6, for example, are electrical wires that carry bits of data between the components. Memory 4 may include an array of dynamic random access memory (DRAM) chips, and store program and data that CPU 2 uses in execution. The system components may also include input/output (I/O) controllers and adapters connected to the CPU 2 and memory 4 via a bus, e.g., I/O bus and connect to I/O devices. For example, display/graphic adapter connects 8 a monitor 28 or another display device/terminal; disk controller 10 connects hard disks 24, for example, for permanent storage; serial controller 12 such as universal serial bus (USB) controller may connect input devices such as keyboard 22 and mouse 20, output devices such as printers 26; network adapter 14 connects the system to another network, for example, to other machines. The system may also include expansion slots to accommodate other devices to connect to the system. For example, a hard disk 24 may store the program of instructions and data that implement the above described methods and systems, which may be loaded into the memory 4, then into the CPU's storage (e.g., caches and registers) for execution by the CPU (e.g., ALU and/or other combination circuit or logic). In another aspect, all or some of the program of instructions and data implementing the above described methods and systems may be accessed, and or executed over the network 18 at another computer system or device. FIG. 18 is only one example of a computer system. The computer system that may implement the methodologies or system of the present disclosure is not limited to the configuration shown in FIG. 18. Rather, another computer system may implement the methodologies of the present disclosure, for example, including but not limited to special processors such as field programmable gate array (FPGA) and accelerators.

In one embodiment, the present invention may be embodied as a computer program product that may include a computer readable storage medium (or media) and/or a computer readable storage medium. Such computer readable storage medium may store computer readable program instructions for causing a processor to carry out one or more methodologies described here. In one embodiment, the computer readable storage medium includes a tangible device that can retain and store instructions for use by an instruction execution device. Examples of the computer readable storage medium may include, but is not limited to, an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples.

The terms "computer system" as may be used in the present application may include a variety of combinations of fixed and/or portable computer hardware, software, peripherals, mobile, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and/or server. A module may be a component of a device, software, program, or system that implements some "functionality", which can be embodied as software, hardware, firmware, electronic circuitry, or etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The embodiments described above are illustrative examples and it should not be construed that the present invention is limited to these particular embodiments. Thus, various changes and modifications may be effected by one skilled in the art without departing from the spirit or scope of the invention as defined in the appended claims.

I claim:

1. A method of providing a diagram based visual procedure note writing, comprising:
   receiving a selection of an image representing a structure from among a plurality of images representing a plurality of structures;
   in response to receiving the selection:
      controlling a user interface to display the selected image in a first container of the user interface, wherein the user interface comprises the first container and a second container;
      selecting a plurality of objects related to the structure represented by the selected image, the plurality of objects comprises texts specifying a plurality of pathological lesions; and
      controlling the user interface to display the selected plurality of objects in the second container of the user interface, wherein the plurality of objects are movable from the second container to the first container displaying the selected image;
   detecting an object among the displayed plurality of objects being moved from the second container to a region in the first container associated with a location within the structure represented by the selected image;
   associating the moved object with the location within the structure represented by the selected image;
   based on the association of the moved object with the location within the structure represented by the selected image:
      selecting a sentence model from among a plurality of sentence models; and
      selecting and updating metadata associated with the selected sentence model;
   controlling the user interface to display a description window overlaying the selected image in the first container, wherein the description window displays a menu of information associated with a pathological lesion specified by the moved object, the description window comprising at least one input field configured to receive user input to further update the selected and updated metadata associated with the selected sentence model;
   composing a sentence based on the selected sentence model, and based on the selected and the updated metadata associated with the selected sentence model, the sentence being a part of a note being displayed in the description window;
   detecting a hover over on the moved object in the first container;
   in response to detecting the hover over:
      outputting a plurality of photographs in the first container of the user interface in a particular order, wherein the plurality of photographs illustrates different locations within the structure represented by the selected image, and the particular order is based on a path in which the plurality of photographs is captured from the different locations within the structure;
   selecting at least one photograph that illustrates the location within the structure among the plurality of photographs, wherein the at least one selected photograph relates to the moved object; and
   assigning the at least one selected photograph as a part of the metadata of the object to further update the updated metadata.

2. The method of claim 1, wherein the structure includes an anatomical structure.

3. The method of claim 1, wherein composing the sentence comprises composing the sentence in real time responsive to receiving an input updating the metadata associated with the selected sentence model.

4. The method of claim 1, wherein the plurality of images, the plurality of objects, and a plurality of locations within the structure, are stored in a knowledgebase as a hierarchically organized data structure, and the hierarchically organized data structure comprises:
   a first level that stores the plurality of images representing the plurality of structures;
   a second level that stores tab representations of the plurality of objects;
   a third level that stores objects; and
   a fourth level that stores the plurality of locations within the structure.

5. The method of claim 1,
   wherein the plurality of images and the plurality of objects are stored in a knowledgebase, and
   wherein selecting the plurality of objects comprises identifying mappings between the selected image and the plurality of objects in the knowledgebase.

6. The method of claim 1,
   wherein the plurality of objects and a plurality of locations within the structure are stored in a knowledgebase, and
   wherein associating the moved object with the location within the structure comprises identifying mappings between the moved object and the location within the structure in the knowledgebase.

7. The method of claim 1, wherein selecting at least one photograph that illustrates the location within the structure among the plurality of photographs is performed in response to:
   receiving a user selection that selects the at least one photograph among the plurality of photographs.

8. A diagram based visual procedure note writing user interface system, comprising:
   a memory device storing a knowledgebase comprising a plurality of images representing a plurality of structures, a plurality of objects related to the plurality of structures, and a plurality of locations within each structure among the plurality of structures; and
   a processor coupled to the memory device and operable to:
   receive a selection of an image representing a structure from among the plurality of images;
   in response to the receipt of the selection:
      control a user interface to display the selected image in a first container of the user interface, wherein the user interface comprises the first container and a second container;
      select a set of objects from among the plurality of objects, the selected set of objects being related to the structure represented by the selected image, the plurality of objects comprises texts specifying a plurality of pathological lesions; and control the user interface to display the selected set of objects in the second container of the user interface, wherein the set of objects are movable from the second container to the first container displaying the selected image;

detect an object among the displayed set of objects being moved from the second container to a region in the first container associated with a location within the structure represented by the selected image;

associate the moved object with the location within the structure represented by the selected image;

based on the association of the moved object with the location within the structure represented by the selected image:
  select a sentence model from among a plurality of sentence models; and
  select and update metadata associated with the selected sentence model;

controlling the user interface to display a description window overlaying the selected image in the first container, wherein the description window displays a menu of information associated with a pathological lesion specified by the moved object, the description window comprising at least one input field configured to receive user input to further update the selected and updated metadata associated with the selected sentence model;

compose a sentence based on the selected sentence model, and based on the selected and the updated metadata associated with the selected sentence model, the sentence being a part of a note being displayed in the description window;

detect a hover over on the moved object in the first container;

in response to the detection of the hover over:
  output a plurality of photographs in the first container of the user interface in a particular order, wherein the plurality of photographs illustrates different locations within the structure represented by the selected image, and the particular order is based on a path in which the plurality of photographs is captured from the different locations within the structure;
  select at least one photograph that illustrates the location within the structure among the plurality of photographs, wherein the at least one selected photograph relates to the moved object; and
  assign the at least one selected photograph as a part of the metadata of the object to further update the updated metadata.

9. The system of claim 8, wherein the processor is operable to compose the sentence in real time responsive to receiving an input updating the metadata associated with the selected sentence model.

10. The system of claim 8, wherein the knowledgebase stores the plurality of images, the plurality of objects, and the plurality of locations within the structure, in a hierarchically organized data structure, and the hierarchically organized data structure comprises:
  a first level that stores the plurality of images representing the plurality of structures;
  a second level that stores tab representations of the plurality of objects;
  a third level that stores objects; and
  a fourth level that stores the plurality of locations within the structure.

11. The system of claim 8, wherein the processor is operable to:
  select the plurality of objects based on an identification of mappings between the selected image and the plurality of objects in the knowledgebase; and
  associate the moved object with the location within the structure based on an identification of mappings between the moved object and the location within the structure in the knowledgebase.

12. The system of claim 8, wherein the processor is operable to:
  control the user interface to display the description window overlaying the selected image in the first container, wherein the description window displays the metadata selected based on the association of the moved object with the location within the structure represented by the selected image.

13. A non-transitory computer readable storage medium storing a program of instructions executable by a machine to perform a method of providing a diagram based visual procedure note writing, the method comprising:
  receiving a selection of an image representing a structure from among a plurality of images representing a plurality of structures;
  in response to receiving the selection:
    controlling a user interface to display the selected image in a first container of the user interface, wherein the user interface comprises the first container and a second container;
    selecting a plurality of objects related to the structure represented by the selected image, the plurality of objects comprises texts specifying a plurality of pathological lesions; and
    controlling the user interface to display the selected plurality of objects in the second container of the user interface, wherein the plurality of objects are movable from the second container to the first container displaying the selected image;
  detecting an object among the displayed plurality of objects being moved from the second container to a region in the first container associated with a location within the structure represented by the selected image;
  associating the moved object with the location within the structure represented by the selected image;
  based on the association of the moved object with the location within the structure represented by the selected image:
    selecting a sentence model from among a plurality of sentence models; and
    selecting and updating metadata associated with the selected sentence model;
  controlling the user interface to display a description window overlaying the selected image in the first container, wherein the description window displays a menu of information associated with a pathological lesion specified by the moved object, the description window comprising at least one input field configured to receive user input to further update the selected and updated metadata associated with the selected sentence model;
  composing a sentence based on the selected sentence model, and based on the selected and the updated metadata associated with the selected sentence model, the sentence being a part of a note being displayed in the description window;
  detecting a hover over on the moved object in the first container;

in response to detecting the hover over:
- outputting a plurality of photographs in the first container of the user interface in a particular order, wherein the plurality of photographs illustrates different locations within the structure represented by the selected image, and the particular order is based on a path in which the plurality of photographs is captured from the different locations within the structure;
- selecting at least one photograph that illustrates the location within the structure among the plurality of photographs, wherein the at least one selected photograph relates to the moved object; and assigning the at least one selected photograph as a part of the metadata of the object to further update the updated metadata.

14. The non-transitory computer readable storage medium of claim 13, wherein composing the sentence comprises composing the sentence in real time responsive to receiving an input updating the metadata associated with the selected sentence model.

15. The non-transitory computer readable storage medium of claim 13, wherein the plurality of images, the plurality of objects, and a plurality of locations within the structure, are stored in a knowledgebase as a hierarchically organized data structure, and the hierarchically organized data structure comprises:
- a first level that stores the plurality of images representing the plurality of structures;
- a second level that stores tab representations of the plurality of objects;
- a third level that stores objects; and
- a fourth level that stores the plurality of locations within the structure.

* * * * *